(12) United States Patent
Bastian et al.

(10) Patent No.: US 7,253,181 B2
(45) Date of Patent: Aug. 7, 2007

(54) β₃ ADRENERGIC AGONISTS

(75) Inventors: Jolie Anne Bastian, Beech Grove, IN (US); Gerd Ruehter, Hamburg (DE); Daniel Jon Sall, Greenwood, IN (US); Theo Schotten, Vierhoefen (DE)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/276,192

(22) Filed: Feb. 17, 2006

(65) Prior Publication Data

US 2006/0142327 A1 Jun. 29, 2006

Related U.S. Application Data

(62) Division of application No. 10/495,133, filed as application No. PCT/US02/33625 on Nov. 12, 2002, now Pat. No. 7,071,208.

(60) Provisional application No. 60/334,031, filed on Nov. 20, 2001.

(51) Int. Cl.
*A61K 31/44* (2006.01)
*C07D 471/04* (2006.01)

(52) U.S. Cl. .................. 514/300; 546/113
(58) Field of Classification Search ............. 546/113; 514/300

See application file for complete search history.

(56) References Cited

U.S. PATENT DOCUMENTS

| | | | |
|---|---|---|---|
| 4,234,595 A | 11/1980 | Kreighbaum et al. |
| 4,276,304 A | 6/1981 | Ikezaki et al. |
| 4,314,943 A | 2/1982 | Kreighbaum et al. |
| 4,826,847 A | 5/1989 | Michel et al. |
| 5,808,080 A | 9/1998 | Bell et al. |
| 6,011,048 A | 1/2000 | Mathvink et al. |
| 6,911,463 B2 | 6/2005 | Sall et al. |
| 7,087,635 B2 | 8/2006 | Sall et al. |
| 2005/0020617 A1 | 1/2005 | Bastian et al. |
| 2005/0080110 A1 | 4/2005 | Sall et al. |
| 2006/0142328 A1 | 6/2006 | Bastian et al. |
| 2006/0142329 A1 | 6/2006 | Bastian et al. |

FOREIGN PATENT DOCUMENTS

| | | |
|---|---|---|
| EP | 0 166 331 | 1/1986 |
| EP | 0 221 414 | 5/1987 |
| EP | 0 236 624 | 9/1987 |
| EP | 0 611 003 | 8/1994 |
| EP | 0 678 511 | 10/1995 |
| EP | 0 764 640 | 3/1997 |
| GB | 2001633 | 2/1979 |
| GB | 1 549 945 | 8/1979 |
| WO | WO 95/29159 | 11/1995 |
| WO | WO 97/10825 | 3/1997 |
| WO | WO 97/46556 | 12/1997 |
| WO | WO 98/04526 | 2/1998 |
| WO | WO 98/09625 | 3/1998 |
| WO | WO 98/32753 | 7/1998 |
| WO | WO 00/40560 | 7/2000 |
| WO | WO 00/44721 | 8/2000 |
| WO | WO 01/07026 | 2/2001 |
| WO | WO 01/35947 | 5/2001 |
| WO | WO 01/36412 | 5/2001 |
| WO | WO 01/53298 | 7/2001 |
| WO | WO 02/06276 | 1/2002 |
| WO | WO 02/38543 | 5/2002 |
| WO | WO 03/016276 | 2/2003 |
| WO | WO 03/016307 | 2/2003 |

OTHER PUBLICATIONS

Shuker, et al., "The application of high-throughput synthesis and purification to the preparation of ethanolamines," *Tetrahedron Letters*, vol. 38, No. 35, pp. 6149-6152.

Weber, et al., "Potent, selective benzenesulfonamide agonists of human b3 adrenergic receptor," *Bioorganic & Medicinal Chemistry letters*, vol. 8, No. 9, pp. 1101-1106 (1998).

Weber, et al., "3-Pyridyloxypropanolamine agonists of the b3 adrenergic receptor with improved pharmacokinetic properties," *Bioorganic & Medicinal Chemistry Letters*, vol. 8, No. 16, pp. 2111-2116 (1998).

*Primary Examiner*—Patricia L. Morris
(74) *Attorney, Agent, or Firm*—John C. Demeter; Gilbert T. Voy

(57) ABSTRACT

The present invention relates to pyrrolopyridine-3-yl group containing β₃ adrenergic receptor agonists or pharmaceutical salts thereof.

6 Claims, No Drawings

β₃ ADRENERGIC AGONISTS

This application is a divisional under 35 U.S.C. Section 121 of U.S. patent application Ser. No. 10/495,133, filed May 7, 2004, now U.S. Pat. No. 7,071,208 B2, which is a national phase application under 35 U.S.C. Section 371 for PCT/US02/33625, filed Nov. 12, 2002, which claims the benefit under 35 U.S.C. Section 119(e) of U.S. provisional patent application 60/334,031, filed Nov. 20, 2001.

The current preferred treatment for Type 2, non-insulin dependent diabetes as well as obesity is diet and exercise, with a view toward weight reduction and improved insulin sensitivity. Patient compliance, however, is usually poor. The problem is compounded by the fact that there are currently no approved medications that adequately treat both Type 2 diabetes or obesity.

One therapeutic opportunity that has recently been recognized involves the relationship between adrenergic receptor stimulation and anti-hyperglycemic effects. Compounds that act as β₃ receptor agonists have been shown to exhibit a marked effect on lipolysis, thermogenesis and serum glucose levels in animal models of Type 2 (non-insulin dependent) diabetes. The β₃ receptor, which is found in several types of human tissue including human fat tissue, has roughly 50% homology to the β₁ and β₂ receptor subtypes yet is considerably less abundant. Stimulation of the β₁ and β₂ receptors can cause adverse effects such as tachycardia, arrhythmia, or tremors. An agonist that is selective for the β₃ receptor over the β₁ and β₂ receptors is, therefore, more desirable for treating Type 2 diabetes or obesity relative to a non-selective agonist.

However, recent studies have suggested the presence of an atypical β receptor associated with atrial tachycardia in rats (*Br. J. of Pharmacol.*, 118:2085-2098, 1996). In other words, compounds that are not agonists of the β₁ and β₂ receptors can still modulate tachycardia through activation of a yet to be discovered β₄ or through some other unknown pathway.

U.S. Pat. No. 5,001,132 discloses certain N-([imidazo[1,2-a]pyridinyl]ethyl)-1-phenoxypropan-2-ol amines as therapeutics for the treatment of glaucoma, i.e., said compounds are beta-blocking agents.

A large number of more recent publications have appeared in recent years reporting success in discovery of agents that stimulate the β₃ receptor. Despite these recent developments, there remains a need to develop a selective β₃ receptor agonist which has minimal agonist activity against the β₁ and β₂ receptors.

The present invention relates to a compound of formula I:

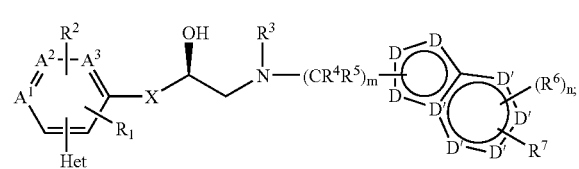

I wherein:
m is 1, 2, 3, 4 or 5;
n is 0, 1 or 2;
$A^1$, $A^2$ and $A^3$ are carbon or nitrogen provided that only one of $A^1$, $A^2$ and $A^3$ can be nitrogen;
each D is either carbon or nitrogen provided that at least one D must be nitrogen;
each D' is either carbon or nitrogen provided that only one D' can be nitrogen;
and further provided that the total number of D and D' that are nitrogen must be two and only two;
Het is an optionally substituted, optionally benzofused 5 or 6 membered heterocyclic ring;
$R^1$ and $R^2$ are independently H, halo, hydroxy, $C_1$-$C_6$ alkyl, $C_1$-$C_6$ alkoxy, $C_1$-$C_4$ haloalkyl, or $SO_2(C_1$-$C_6$ alkyl);
$R^3$ is H or $C_1$-$C_6$ alkyl;
$R^4$ and $R^5$ are independently at each occurrence H or $C_1$-$C_6$ alkyl; or $R^4$ and $R^5$ combine with the carbon to which they are both attached to form a $C_3$-$C_7$ carbocyclic ring;
$R^6$ is independently at each occurrence halo, hydroxy, cyano, $C_1$-$C_6$ alkyl, $C_1$-$C_4$ haloalkyl or $C_1$-$C_6$ alkoxy;
$R^7$ is H, $CO_2R^8$, $CONR^8R^8$, CH=$CHR^9$, $CH_2CH_2R^9$, $NR^8R^8$, $NR^8SO_2R^8$, $O(CR^{10}R^{11})_pR^{12}$, $O(CR^{10}R^{11})_qR^{13}$, $SO_2R^8$, $SO_2NR^8R^8$, optionally substituted phenyl or optionally substituted heterocycle;
X is absent or is $OCH_2$ or $SCH_2$;
p is 0, 1, 2 or 3;
q is 1, 2 or 3;
$R^8$ is independently at each occurrence H, $C_1$-$C_6$ alkyl or phenyl; or when two $R^8$ moieties are connected to the same nitrogen atom, then said $R^8$ moieties may combine with the nitrogen to which they are attached to form a pyrollidinyl, piperidinyl, morpholinyl or hexamethyleneimino ring;
$R^9$ is cyano, $CO_2R^{14}$, $CONR^{14}R^{14}$, $CONR^{14}SO_2R^{14}$, $SO_2R^{14}$, heterocycle or optionally substituted phenyl;
$R^{10}$ and $R^{11}$ are independently at each occurrence H or $C_1$-$C_6$ alkyl;
$R^{12}$ is hydrogen, $CO_2R^{15}$, $CONR^{15}R^{15}$, $SO_2R^{15}$, $SO_2NR^{16}R^{16}$, optionally substituted phenyl or optionally substituted heterocycle,
$R^{13}$ is cyano, $NR^{16}R^{16}$, $NR^{16}SO_2R^{16}$ or $OR^{16}$;
$R^{14}$, $R^{15}$ and $R^{16}$ are independently at each occurrence H, $C_1$-$C_6$ alkyl or phenyl; or when two $R^{14}$ or two $R^{15}$ or two $R^{16}$ moieties are connected to the same nitrogen atom, then said $R^{14}$ or $R^{15}$ or $R^{16}$ moieties may combine with the nitrogen to which they are attached to form a pyrollidinyl, piperidinyl, morpholinyl or hexamethyleneimino ring; or a pharmaceutical salt thereof.

The present invention also relates to processes for preparing, as well as pharmaceutical formulations containing a compound of formula I. In another embodiment, the pharmaceutical formulations of the present invention may be adapted for use in treating Type 2 diabetes and obesity and for agonizing the β₃ receptor.

The present invention also relates to methods for treating Type 2 diabetes and obesity, as well as a method for agonizing the β₃ receptor employing a compound of formula I.

In addition, the present invention relates to a compound of formula I for use in treating Type 2 diabetes and obesity as well as a compound of formula I for use in agonizing the β₃ receptor. The present invention is further related to the use of a compound of formula I for the manufacture of a medicament for treating Type 2 diabetes and obesity as well as for agonizing the β₃ receptor.

For the purposes of the present invention, as disclosed and claimed herein, the following terms are defined below.

The term "halo" represents fluoro, chloro, bromo, or iodo.
The term "$C_1$-$C_6$ alkyl" represents a straight, branched or cyclic hydrocarbon moiety having from one to six carbon atoms, e.g., methyl, ethyl, n-propyl, isopropyl, cyclopropyl, n-butyl, isobutyl, sec-butyl, t-butyl, cyclobutyl, pentyl, cyclopentyl, hexyl, cyclohexyl and the like. The term "$C_1$-$C_4$ alkyl" refers specifically to methyl, ethyl, n-propyl, isopropyl, cyclopropyl, n-butyl, isobutyl, sec-butyl, t-butyl and cyclobutyl. A "$C_1$-$C_4$ haloalkyl" group is a $C_1$-$C_4$ alkyl moiety substituted with up to six halo atoms, preferably one to three halo atoms. An example of a haloalkyl group is trifluoromethyl. A "$C_1$-$C_6$ alkoxy" group is a $C_1$-$C_6$ alkyl moiety connected through an oxy linkage.

The term "$C_3$-$C_7$ carbocyclic ring" refers specifically to a cyclopropyl, cyclobutyl, cyclopentyl, cyclohexyl and cycloheptyl ring.

The term "optionally substituted" as used herein means an optional substitution of one to three, preferably one or two groups independently selected from halo, hydroxy, oxo, cyano, nitro, phenyl, benzyl, $C_1$-$C_6$ alkyl, $C_1$-$C_4$ haloalkyl, $C_1$-$C_6$ alkoxy, $COR^{17}$, $CONR^{17}R^{17}$, $CO_2R^{17}$, $NR^{17}R^{17}$, $NR^{17}COR^{18}$, $NR^{17}SO_2R^{18}$, $OCOR^{18}$, $OCO_2R^{17}$, $OCONR^{17}R^{17}$, $SR^{17}$, $SOR^{18}$, $SO_2R^{18}$ and $SO_2(NR^{17}R^{17})$, where $R^{17}$ is independently at each occurrence H, $C_1$-$C_6$ alkyl, phenyl or benzyl and $R^{18}$ is independently at each occurrence $C_1$-$C_6$ alkyl, phenyl or benzyl.

The terms "heterocycle" and "heterocyclic" represent a stable, saturated, partially unsaturated, fully unsaturated or aromatic 5 or 6 membered ring, said ring having from one to four heteroatoms that are independently selected from the group consisting of sulfur, oxygen, and nitrogen. The heterocycle may be attached at any point which affords a stable structure. Representative heterocycles include 1,3-dioxolane, 4,5-dihydrooxazole, furan, imidazole, imidazolidine, isothiazole, isoxazole, morpholine, oxadiazole, oxazole, oxazolidinedione, oxazolidone, piperazine, piperidine, pyrazine, pyrazole, pyrazoline, pyridazine, pyridine, pyrimidine, pyrrole, pyrrolidine, tetrazole, thiadiazole, thiazole, thiophene and triazole. Representative "benzofused" heterocycles include benzoxazole, benzimidazole, benzofuran, benzothiophene, benzothiazole, azaindole, and indole. Further specific examples of benzofused and non-benzofused heterocycles are described below in the Preparations and Examples sections.

In the compound of formula I, the following moiety is found:

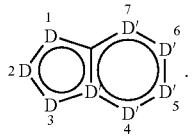

This moiety represents a 6,5 heteroaromatic fused bicyclic ring system and is sometimes referred to herein as the "6,5 ring system". The two circles used in the structure of this moiety have been used to connote that this bicyclic ring system is aromatic. The numbers on the perimeter of the pictured moiety represent the numbering system used in the claims and preferred embodiments to describe positions of substituents off of the 6,5 ring system and/or connectivity onto said system.

The term "suitable solvent" refers to any solvent, or mixture of solvents, inert to the ongoing reaction that sufficiently solubilizes the reactants to afford a medium within which to effect the desired reaction.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The preferred patient of treatment is a human.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

The terms "preventing", "prevention of", "prophylaxis", "prophylactic" and "prevent" are used herein interchangeably and refer to reducing the likelihood that the recipient of a compound of formula I will incur or develop any of the pathological conditions, or sequela thereof, described herein.

As used herein, the term "effective amount" means an amount of a compound of formula I that is capable of treating conditions, or detrimental effects thereof, described herein or that is capable of agonizing the $\beta_3$ receptor.

The term "selective $\beta_3$ receptor agonist" means a compound that displays preferential agonism of the $\beta_3$ receptor over agonism of the $\beta_1$ or $\beta_2$ receptor. Thus, $\beta_3$ selective compounds behave as agonists for the $\beta_3$ receptor at lower concentrations than that required for similar agonism at the $\beta_1$ and $\beta_2$ receptors. A $\beta_3$ selective compound also includes compounds that behave as agonists for the $\beta_3$ receptor and as antagonists for the $\beta_1$ and $\beta_2$ receptors.

The term "pharmaceutical" when used herein as an adjective means substantially non-deleterious to the recipient patient.

The term "formulation", as in pharmaceutical formulation, is intended to encompass a product comprising the active ingredient(s) (compound of formula I), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing a compound of the present invention and a pharmaceutical carrier.

The term "unit dosage form" refers to physically discrete units suitable as unitary dosages for human subjects and other non-human animals (as described above), each unit containing a predetermined quantity of active material calculated to produce the desired therapeutic effect, in association with a suitable pharmaceutical carrier.

Because certain compounds of the invention contain an acidic moiety (e.g., carboxy), the compound of formula I may exist as a pharmaceutical base addition salt thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like.

Because certain compounds of the invention contain a basic moiety (e.g., amino), the compound of formula I can also exist as a pharmaceutical acid addition salt. Such salts include the salicylate, sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propionate, oxalate, malonate, succinate, suberate, sebacate, fumarate, maleate, 2-butyne-1,4 dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and like salts. Preferred acid addition salts include the hydrochloride and glycolate salts.

PREFERRED COMPOUNDS (EMBODIMENTS) OF THE INVENTION

Certain compounds of the invention are particularly interesting and are preferred. The following listing sets out several groups of preferred compounds. It will be understood that each of the listings may be combined with other listings to create additional groups of preferred compounds.
a) m is 2;
b) n is 0 or 1;
c) n is 0;
d) $A^1$, $A^2$ and $A^3$ are carbon;
e) the 6,5 ring system is of the formula:

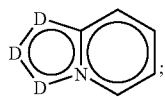

f) the 6,5 ring system is of the formula:

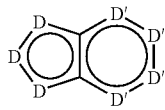

where only one D can be nitrogen;
g) the 6,5 ring system is of the formula:

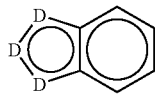

h) the 6,5 ring system is 7-azaindole connected to the $(CR^4R^5)_n$ moiety at the 3-position of the azaindole ring system;
i) the 6,5 ring system is 7-azaindole connected to the $(CR^4R^5)_n$ moiety at the 3-position of the azaindole ring system; n is 0; and $R^7$ is H;
j) the 6,5 ring system is imidazo[1,5-a]pyridine and is connected to the $(CR^4R^5)_n$ moiety at the n imidazo[1,5-a]pyridine ring system;
k) the 6,5 ring system is imidazo[1,2-a]pyridine and is connected to the $(CR^4R^5)_n$ moiety at the 3-position of the imidazo[1,2-a]pyridine ring system;
l) Het is at the ortho-position relative to X;
m) Het is an optionally substituted 5-membered, non-benzofused ring containing one or two heteroatoms that are independently selected from the group consisting of sulfur, oxygen, and nitrogen;
n) Het is selected from isoxazole; thiophene; and pyrrole; wherein said Het moieties are optionally substituted once with chloro, fluoro, cyano, methyl or $COCH_3$;
o) Het is isoxazol-3-yl or thien-2-yl wherein said thien-2-yl moiety is optionally substituted once with chloro, fluoro, cyano, methyl or $COCH_3$;
p) Het is isoxazol-3-yl or thien-2-yl wherein said thien-2-yl moiety is optionally substituted once with $COCH_3$;
q) Het is thien-2-yl;
r) $R^1$ is H;
s) $R^2$ is H;
t) $R^3$ is H;
u) $R^4$ and $R^5$ are independently H or methyl at each occurrence;
v) the moiety $(CR^4R^5)_m$ is $C(CH_3)_2CH_2$;
w) $R^6$ is methyl at each occurrence;
x) $R^7$ is at the 6- or 7-position of the 6,5 ring system to which it is attached;
y) $R^7$ is at the 7-position of the 6,5 ring system to which it is attached
z) $R^7$ is H, $O(CH_2)_pR^{12}$ or optionally substituted heterocycle; p is 0 or 1; and $R^{12}$ is $CONR^{15}R^{15}$, optionally substituted phenyl or optionally substituted heterocycle;
aa) $R^7$ is H;
bb) $R^7$ is $O(CH_2)_pR^{12}$; p is 0 or 1; and $R^{12}$ is $CONR^{15}R^{15}$, phenyl or pyridyl substituted once with $CONR^{17}R^{17}$, where $R^{17}$ is independently at each occurrence H or $C_1$-$C_6$ alkyl;
cc) $R^7$ is thienyl;
dd) X is $OCH_2$;
ee) $R^{15}$ and $R^{17}$ are hydrogen at each occurrence;
ff) the compound of formula I is an acid addition salt;
gg) the compound of formula I is the hydrochloride salt.

Synthesis

The compound of formula I may be prepared as described in the following Schemes and Examples.

Scheme 1

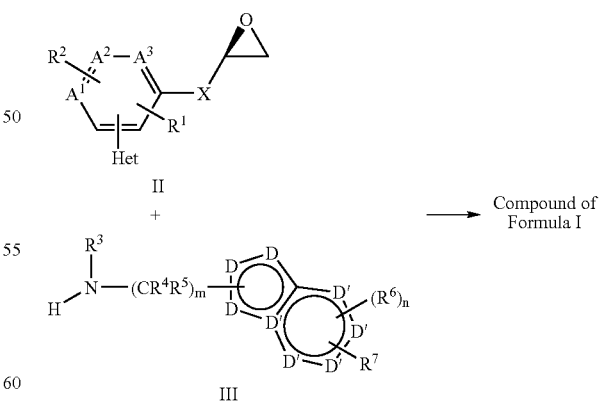

The reaction of Scheme 1 may be carried out under conditions appreciated in the art for the amination of epoxides. For example, the epoxide of formula II may be combined with an amine of formula III in a lower alcohol, dimethylformamide or dimethylsulfoxide, preferably ethanol, isopropanol, n-butanol or t-butanol, at room temperature to the reflux temperature of the reaction mixture, preferably between 40° C.-90° C. The reaction may also be carried out tinder conditions generally described in Atkins, et al., *Tet. Let.*, 27:2451, 1986. These conditions include mixing the reagents in the presence of trimethylsilyl acetamide in a polar aprotic solvent such as acetonitrile, dimethylformamide, acetone, dimethylsulfoxide, dioxane, diethylene glycol dimethyl ether, tetrahydrofuran, or other polar aprotic solvents in which the reagents are soluble.

The compound of formula I may also be prepared via a Suzuki coupling reaction as shown in Scheme 2.

Compounds of the formula Het-B(OH)$_2$ are either commercially available, known in the art, or can be prepared by methods known in the art or described herein.

Preparations

Epoxides of Formula II and IV

Epoxides 1-6 are prepared for use as described in Scheme 1. These epoxides are pictured below in Table 1.

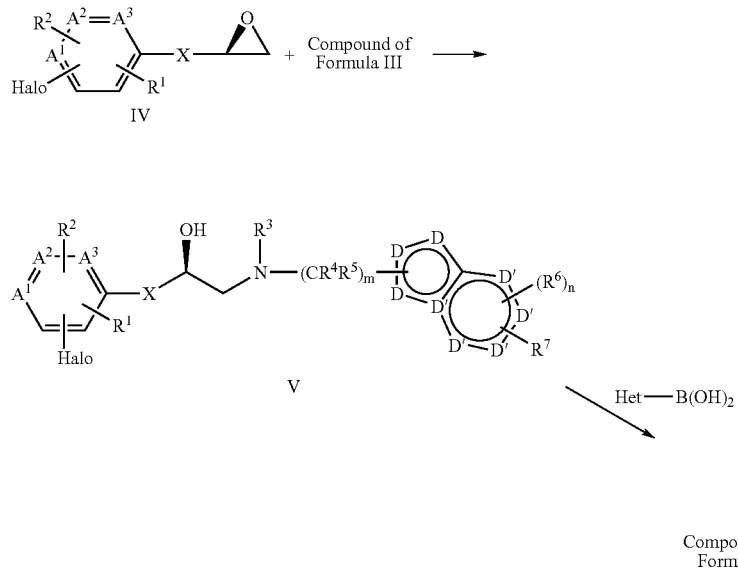

A compound of formula IV may be reacted with a compound of formula III as described above in Scheme 1. The compound of formula V (an aryl halide) may then be reacted with a heteroaryl boronic acid, an aryl boronic ester, or an aryl boronic cyclic ester, preferably an aryl boronic acid, under conditions appreciated in the art for the coupling of aromatic halides with aryl boronic acids and their derivatives. This coupling is known in the art generally as a Suzuki coupling. The skilled artisan will recognize that an aryl triflate may also be employed in the present Suzuki coupling as an alternative to employing an aryl halide.

The epoxide starting materials employed in Schemes 1 and 2 may be prepared by techniques recognized and appreciated by one skilled in the art. See, e.g., U.S. Pat. No. 4,663,334; European Patent Application 171209; Korn, et al., *J. Pharm. Sci.*, 69(9):1010-13, 1980; and PCT Patent Application No. PCT/US01/16519, filed Jul. 9, 2001 and references cited below in the Preparations section for representative and/or analogous procedures for preparing the epoxides of formula II and IV.

The amines of formula III employed in Scheme 1 may also be prepared by techniques recognized and appreciated by one skilled in the art. See, e.g., the Preparations below or the references cited therein for representative and/or analogous procedures for preparing the amines of formula III.

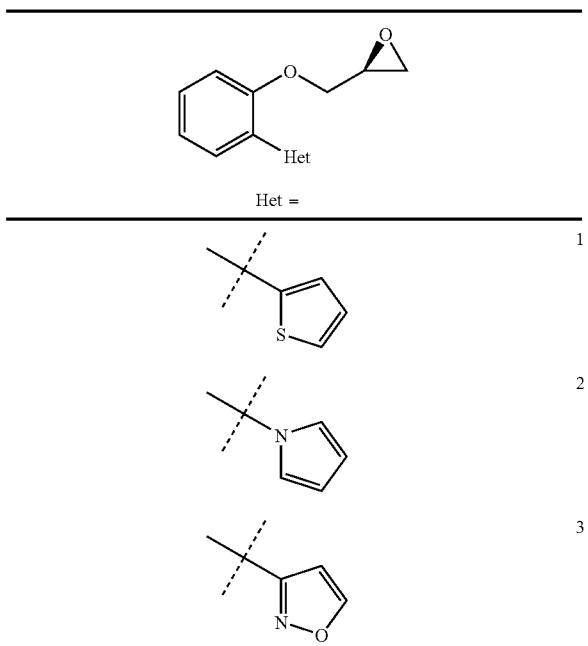

TABLE 1-continued

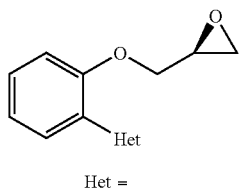

Het =

| |
|---|
| 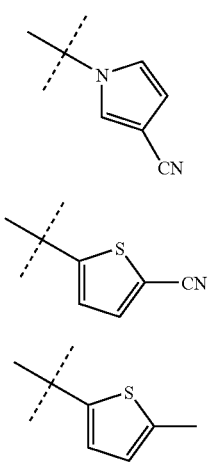 4 |
| 5 |
| 6 |

Epoxide 1

A mixture of 2-(thien-2-yl)phenol (*J. Heterocycl. Chem.*, 22(6):1667-9, 1985; 1 equivalent), (2S)-glycidyl 3-nitrobenzenesulfonate (1.2 equivalents), potassium carbonate (1.2 equivalents) and acetone are refluxed for 16 hours, cooled to room temperature and the solids removed via filtration. The filtrate is concentrated and the crude product purified on silica gel (ethyl acetate/hexane) to give the title epoxide.

Epoxides 2 and 3

2-(Pyrrol-1-yl)phenol (*J. Het. Chem.*, 8:283-287, 1971) and 2-(isoxazol-3-yl)phenol (*J. Het. Chem.*, 8:283-287, 1971) are reacted with (2S)-glycidyl 3-nitrobenzenesulfonate substantially as described for Epoxide 1 to yield the title epoxides.

Epoxide 4

2-(3-Formyl-1-pyrrolyl)phenol (3 g, 16 mmol) and triethylamine (17.6 mmol) are added to a suspension of hydroxylamine hydrochloride (1.22 g, 17.6 mmol) in acetic anhydride (7.7 ml), and the mixture is allowed to stir overnight at ambient temperature. The mixture is refluxed for 5 hours, concentrated, dissolved in 50 ml ethanol and stirred for 10 min with 50 ml 2 M aqueous sodium hydroxide. After neutralisation with aqueous hydrochloric acid, and extraction with ethyl acetate, the organic layer is dried and concentrated. The residue is purified by chromatography (toluene/ethanol 9:1) to yield 2-(3-cyano-1-pyrrolyl)phenol (2.4 g, 92%). This phenolic product is reacted with (2S)-glycidyl 3-nitrobenzenesulfonate substantially as described for Epoxide 1 to yield the title epoxide.

Epoxide 5

A solution of 5-bromothiophene-2-carbonitrile (1.25 g, 6.65 mmol) in 50 ml of dioxane is degassed with argon, tetralkis(triphenylphosphine)palladium(0) (768 mg, 0.665 mmol) is added and the mixture is stirred for 5 minutes. 2-Methoxybenzene boronic acid (2.02 g, 13.3 mmol) and aqueous 2 N sodium carbonate (13.3 ml) are successively added and the mixture is stirred for 16 hours at 85° C. Extractive work-up (2×50 ml dichloromethane and 2×30ml water). The organic phase is dried over sodium sulfate, filtrated and evaporated. The residue (4.05 g) is purified via flash chromatography on silica (eluent: 100% hexane>hexane/ethyl acetate 96:4 gradient) to give 1.37 g of 2-(5-cyanothien-2-yl)anisole (96%). M+=215.

An intimate mixture of 2-(5-cyanothien-2-yl)anisole (1.2 g, 5.9 mmol) and pyridinium hydrochloride (13.7 g, 119 mmol) is heated for 1 hour at 210° C. under argon. The mixture is cooled to ambient temperature and a 1:1 mixture of water and ethyl acetate is added to break and dissolve the solid cake formed during the reaction. The slurry is then transferred to a separation funnel and dichloromethane is added until the organic phase had a higher density than the water phase (organic phase=lower phase). The organic phase contains the desired product and is separated. The remaining aqueous phase is additionally extracted twice with dichloromethane and the collected organic phases are dried over sodium sulfate and evaporated. The residue is purified via flash column on silica (eluent: 100% hexane>hexane/ethyl acetate 8:2 gradient) to give 973 mg of 2-(5-cyanothien-2-yl)phenol (87%). M+=201.

To a solution of 2-(5-cyanothien-2-yl)phenol (970 mg, 4.819 mmol) in 20 ml of dry 2-butanone is added (2S)-glycidyl 3-nitrobenzenesulfonate (1.25 g, 4.82 mmol) and potassium carbonate (732 mg, 5.30 mmol) successively. After stirring for 48 hours at 75° C., the mixture is diluted with ethyl acetate and extracted with 2N aqueous sodium hydroxide (2×30 ml) and water (1×30 ml). (M+=257).

Epoxide 6

Epoxide 6 is prepared by a procedure substantially similar to that described for Epoxide 5. The starting halo thiophenes used to prepare Epoxides 5 and 6 are known from the literature, see e.g., *J. Mater. Chem.*, 5(4), 653-61, 1995; *J. Chem. Soc.*, Perkin Trans. 2, 5:625-30, 1982; *Chem. Scr.*, 5(5), 217-26, 1974; *Bull. Soc. Chim. Fr.*, 11:4115-20, 1967; *Bull. Soc. Chim. Fr.*, 11:4121-6, 1967; *Bull. Inst. Chem. Res.*, 52(3):561-5, 1974; *J. Med. Chem.*, 43(16):3168-3185, 2000; *Bioorg. Med. Chem. Lett.*, 10(5):415-418, 2000; and JP 08311060.

Epoxide 7

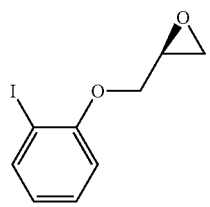

Epoxide 7 is prepared for use as described in Scheme 1. A mixture of 2-iodophenol (5.00 g, 22.7 mmol), 2,3-epoxypropyl-(2S)-3-nitrobenzenesulfonate (5.89 g, 22.7 mmol) and potassium carbonate (3.44 g, 24.9 mmol) in methylethylketone (150 ml) is refluxed for 18 hours. After cooling, the salts are removed by filtration. The filter cake is rinsed thoroughly with dichloromethane and the collected filtrates are evaporated. The residue is purified via flash chromatography on silica gel using a hexane-hexane/ethyl acetate gradient (100 to 90:10).

Amines of Formula III

Amines 1-25 are prepared or are obtained from commercial sources for use schemes 1 or 2. These amines are pictured below in Table 2.

TABLE 2-continued

| | |
|---|---|
| 16 | 24 |
| 18 | 25 |
| 19 | |
| 20 | |
| 21 | |
| 22 | |
| 23 | |

Amine 1

A 0° C. solution of diacetonamine hydrogen oxalate (15 g, 73.1 mmol) in 300 ml of $CH_2Cl_2$ and 35 ml of triethylamine is treated with trifluoroacetic anhydride (10.3 ml, 73.1 mmol). The resulting mixture is allowed to warm to ambient temperature and stir overnight. Excess 1N aqueous HCl is added and the layers are separated. The aqueous layer is extracted with $CH_2Cl_2$ (150 ml), and the combined organic layers are washed with a mixture of water and brine, dried over $Na_2SO_4$ and concentrated in vacuo to an oil. Purification of the crude residue ($SiO_2$; linear gradient of 5 to 50% ethyl acetate in hexanes) affords 4.1 g (19.4 mmol; 27%) of the trifluoroacetic acid amide.

A solution of the amide (4.0 g, 18.9 mmol) in 50 ml of methanol is treated with bromine (970 µl, 18.9 mmol) dropwise. The resulting mixture is allowed to stir at ambient temperature overnight. The reaction mixture is concentrated in vacuo and partitioned between ethyl acetate and water. The organic layer is washed with brine, dried over $Na_2SO_4$ and concentrated in vacuo. Purification of the crude residue ($SiO_2$; linear gradient of 2 to 40% ethyl acetate in hexanes) affords 2.25 g (7.76 mmol; 41%) of the desired α-bromoketone.

A solution of the α-bromoketone (900 mg, 3.1 mmol) and 2-aminopyridine (292 mg, 3.1 mmol) in 15 ml of ethanol is heated overnight at reflux. The reaction mixture is concentrated in vacuo. Purification of the crude imidazopyridine ($SiO_2$; linear gradient of 0 to 5% 2M $NH_3$/methanol in $CHCl_3$) affords 616 mg (2.16 mmol; 70%) of the trifluoroacetic acid amide protected title amine as a pale yellow waxy solid.

A slurry of the protected amine (570 mg, 2.0 mmol) and $K_2CO_3$ (1.4 g, 10 mmol) in 20 ml of methanol and 6 ml of water is heated 2 days at 64° C. The reaction mixture is concentrated in vacuo and partitioned between $CHCl_3$ (20 ml) and water (10 ml). The aqueous layer is extracted with $CHCl_3$ (20 ml). The combined organic layers are dried over $Na_2SO_4$ and concentrated in vacuo. Purification of the crude residue ($SiO_2$; linear gradient of 0 to 10% 2M $NH_3$/methanol in $CHCl_3$) affords 313 mg (1.65 mmol; 83%) of the title amine.

Amine 2

2-(4-Bromo-3-oxo-butyl)-isoindole-1,3-dione is prepared by condensation of but-1-en-3-one with phthalimide followed by bromination according to known procedures (*J. Med. Chem.*, 35:3239, 1992. A solution of 2-(4-bromo-3-oxo-butyl)-isoindole-1,3-dione (8.9 g, 30.06 mmol) and 2-aminopyridine (2.8 g, 29.75 mmol) in ethanol is heated at reflux for 4 hours. The mixture is cooled to room temperature and concentrated. The residue is purified by chromatography (silica gel, dichloromethane/ethanol 95:5); to give 4.23 g of 2-[2-(imidazo[1,2-a]pyridin-2-yl)ethyl]-isoindole-1,3-dione (49%).

A mixture of 2-[2-(imidazo[1,2-a]pyridin-2-yl)ethyl]-isoindole-1,3-dione (4.5 g, 15.45 mmol), 1,2-diaminoethane (25 ml), and isopropanol (125 ml) is heated at reflux at 125° C. for 5 hours. The solvent is removed under reduced pressure and the residue is treated with water (50 ml). The aqueous wash is extracted with dichloromethane (3×50 ml). The combined organic layers are dried over magnesium sulfate and concentrated in vacuo to leave 840 mg of the title amine (34%). (See also, *J. Med. Chem.*, 16:1272, 1973.

Amine 3

A solution of 3,3 dimethylacrylic acid (30 g, 0.3 mol) in 360 ml of 28% aqueous ammonia is heated in an autoclave at 140° C. for 12 hours (internal pressure 15 bar). After cooling and pressure release, the reaction mixture is evaporated to a small volume and dissolved in 60 ml of ethanol. The solution is poured into 150 ml of ice cold tetrahydrofuran. The colorless crystalline precipitate thus obtained is collected by suction and dried at 50° C. for 4 hours in a vacuum oven to give 27.4 g of 3-amino-3-methyl butanoic acid (78%).

An intimate mixture of of 3-amino-3-methyl butanoic acid (27.4 g, 0.234 mol) and phthalic anhydride (38.1 g, 0.257 mol) is heated at 180° C. for 1.5 hours. After cooling, the reaction mixture is dissolved in 40 ml of ethanol and kept in a refrigerator for 54 hours. The colorless crystalline precipitate thus obtained is collected by suction and dried at 50° C. for 3 hours in a vacuum oven to give 19.2 g of β,β-dimethyl-1,3-dioxo-2-isoindolinepropionic acid (58%).

To a solution of β,β-dimethyl-1,3-dioxo-2-isoindolinepropionic acid (5 g, 20.2 mmol) and N,N-dicyclohexylcarbodiimide (4.6 g, 22.24 mmol) in 50 ml of dry methylene chloride is added 2-(aminomethyl)pyridine (2.41 g, 2.3 ml, 22.24 mmol) at ambient temperature. The mixture is stirred for 24 hours. The precipitate of dicyclohexyl urea is filtered off and discarded. The filtrate is evaporated and the residue is purified via flash chromatography on silica gel using a methylene chloride/methylene chloride-ethanolic ammonia gradient (100 to 96:4) to give 3.97 g of N-[(2-pyridinyl)methyl]-1,3-dihydro-β,βdimethyl-1,3-dioxo-2H-isoindole-2-propanamide (58%).

A solution of N-[(2-pyridinyl)methyl]-1,3-dihydro-β,β-dimethyl-1,3-dioxo-2H-isoindole-2-propanamide (1.39 g, 4.12 mmol) in 30 ml of neat phosphoryl chloride is heated to 75° C. for 19 hours. The reaction mixture is poured on crushed ice and extracted with methylene chloride. The organic phase is dried over sodium sulfate and evaporated. The residue is purified via flash chromatography on silica gel using a methylene chloride/methylene chloride-ethanolic ammonia gradient (100 to 96:4) to give 947 mg of 2-(2-imidazo[1,5-a]pyridin-3-yl-2-methyl-propyl)-1H-isoindole-1,3(2H)-dione (72%).

To a solution of 2-(2-imidazo[1,5-a]pyridin-3-yl-2-methyl-propyl)-1H-isoindole-1,3(2H)-dione (1.279 g, 3.98 mmol) in 17 ml of methanol is added hydrazine hydrate (1.39 g, 1.35 ml, 27.84 mmol) and the mixture heated to 100° C. for 15 minutes in a microwave oven (MLS ETHOS 1600). The reaction mixture is evaporated. The residue is purified via flash chromatography on silica gel using a methylene chloride/methylene chloride-ethanolic ammonia gradient (100 to 96:4) to give 355 mg of the title amine (55%).

Amine 4

7-Azaindole (5.05 g, 43 mmol) and Eschenmoser's salt (N,N-dimethylmethyleneammonium iodide; 8.48 g, 45 mmol) are combined in 100 ml of glacial acetic acid. After heating at 65° C. for 1 hour, the reaction mixture is concentrated in vacuo. The resulting solid is triturated with ethyl acetate, filtered and dried in vacuo to give 3-dimethylaminomethyl-1H-7-azaindole hydroiodide in quantitative yield.

A 0° C. solution of 3-dimethylaminomethyl-1H-7-azainidole hydroiodide (10 g, 33 mmol) in 46 ml of methanol and 46 ml of 2-nitropropane is treated with methyl iodide (2.15 ml, 35 mmol) and solid sodium methoxide (3.65 g, 68 mmol) sequentially. The resulting mixture is allowed to warm to ambient temperature, and, after stirring overnight, the reaction mixture is diluted with ethyl acetate (100 ml) and saturated aqueous $NH_4Cl$ solution (100 ml). The aqueous layer is extracted with ethyl acetate (2×100 ml), and the combined organic layers are dried over $Na_2SO_4$ and concentrated in vacuo to give 3-(2-methyl-2-nitropropyl)-1H-7-azaindole in 92% yield.

A solution of 3-(2-methyl-2-nitropropyl)-1H-7-azaindole (2.3 g, 11 mmol) in 200 ml of tetrahydrofuran and 100 ml of ethyl acetate is treated with Raney nickel (2.0 g), and the resulting mixture is heated overnight (60° C.) under an atmosphere of $H_2$ (60 psi). The reaction mixture is filtered over celite and concentrated in vacuo. Purification of the crude residue ($SiO_2$; 10% 2M $NH_3$/methanol in $CHCl_3$) affords 1.0 g (50%) of the title amine.

Amine 5

A 0° C. solution of 1,2-phenylenediamine (925 mg, 8.57 mmol) in 50 ml of toluene is treated with $Al(CH_3)_3$ (2 M solution in toluene; 9.6 ml, 19.2 mmol). After 30 minutes, 4-nitro-4-methylpentanoic acid methyl ester (1.0 g, 5.71 mmol) is added slowly. The resulting mixture is heated to 95° C. and allowed to stir overnight at that temperature. The reaction mixture is cooled to ambient temperature, then quenched with water. The resulting precipitate is filtered, rinsing well with methanol. The filtrate is concentrated in vacuo, and the crude residue is dissolved in 50 ml of tetrahydrofuran and 50 ml of ethyl acetate, Raney nickel is added, and the resulting mixture is heated overnight (60° C.) under an atmosphere of $H_2$ (60 psi). The reaction mixture is filtered over celite and concentrated in vacuo. Purification of the crude residue ($SiO_2$; linear gradient of 0 to 15% 2M $NH_3$/methanol in $CHCl_3$) affords 515 mg (2.53 mmol; 30%) of the title amine.

Amine 6

A 0° C. solution of benzimidazole (3.0 g, 25.4 mmol) in 100 ml of tetrahydrofuran is treated with NaH (60% dispersion in mineral oil; 1.2 g, 30.5 mmol). After 1 hour, (S)-(−)-propylene oxide (3.5 ml, 50.8 mmol) is added, and the resulting mixture is allowed to slowly warm to ambient temperature and stir for 24 hours. The reaction mixture is quenched with $H_2O$ and extracted with ethyl acetate. The organic layer is dried over $Na_2SO_4$ and concentrated in vacuo. Purification of the crude residue (SiO$_2$; ethyl acetate) affords 1.42 g (8.06 mmol; 32%) of the alkylated product.

A 0° C. solution of the alkylated product (1.3 g, 7.38 mmol) in 40 ml of CH$_2$Cl$_2$ and 3.1 ml of triethylamine is treated with methanesulfonyl chloride (1.1 ml, 14.8 mmol). After 1.5 hours, the reaction mixture is diluted with ethyl acetate (100 ml) and 1M aqueous Na$_2$CO$_3$ solution (100 ml). The organic layer is washed with brine, dried over Na$_2$SO$_4$ and concentrated in vacuo. The crude mesylate is dissolved in 40 ml of dimethylformamide, and NaN$_3$ (960 mg, 14.8 mmol) is added. The resulting mixture is heated at 60° C. for 5 hours, then poured into H$_2$O (100 ml) and extracted with ethyl acetate (2×100 ml). The combined organic layers are washed with brine (100 ml), dried over Na$_2$SO$_4$ and concentrated is in vacuo. The crude azide is dissolved in 25 ml of tetrahydrofuran and treated with PPh$_3$ (2.56 g, 9.78 mmol). After stirring at room temperature overnight, the reaction mixture is treated with water (10 ml) and heated at 60° C. for 6 hours to hydrolyze the intermediate aza-ylide. Upon cooling to ambient temperature, the reaction mixture is diluted with ethyl acetate (200 ml) and brine (200 ml). The organic layer is washed with brine (100 ml), dried over Na$_2$SO$_4$ and concentrated in vacuo. Purification of the crude residue by radial chromatography (SiO$_2$; 2.5% step gradient of 0% to 5% 2M NH$_3$/MeOH in CHCl$_3$) affords 527 mg (3.01 mmol; 41%) of the title amine.

Amine 7

4-Methyl-4-nitropentanal is prepared by condensation of acrolein and 2-nitropropane according to a known procedure (Synthesis 1986, 237). To a solution of 4-methyl-4-nitropentanal (8.5 g, 58.56 mmol) in acetic acid (125 ml) is added bromine (9.12 g, 57.07 mmol) dropwise while the temperature is kept below 15° C. After stirring for 15 minutes at room temperature the reaction is poured into a mixture of water and ice (250 ml) and extracted two times with dichloromethane. The combined organic extracts are washed with water and with brine, successively, dried over magnesium sulfate, and the solvent is removed under reduced pressure to leave 10.7 g of 2-bromo-4-methyl-4-nitropentanal which is used for the next step without further purification.

A mixture of 2-amino-3-benzyloxypyridine (2.7 g, 13.5 mmol) and 2-bromo-4-methyl-4-nitropentanal (3.0 g, 13.5 mmol) in ethanol (20 ml) is heated at 100° C. overnight. The solvent is removed under reduced pressure and the residue is treated with saturated aqueous NaHCO$_3$ solution. The aqueous mixture is extracted two times with ethyl acetate. The combined organic extracts are dried over magnesium sulfate and concentrated in vacuo. The residue is chromatographed (silica gel, dichloromethane/ethanol 9:1) to give 2.83 g of 3-(2-methyl-2-nitropropyl)-8-(phenylmethoxy) imidazo[1,2-a]pyridine (64%).

Method A: To a solution of 3-(2-methyl-2-nitropropyl)-8-(phenylmethoxy)imidazo[1,2-a]pyridine (1.1 g, 3.38 mmol) in ethanol (20 ml) is added Raney-Ni (2 g). The mixture is set under an atmosphere of hydrogen and stirred vigorously overnight at room temperature. The catalyst is removed by filtration through Celite and the solvent is distilled off under reduced pressure to leave 850 mg of the title amine (85%).

Method B: A mixture of 3-(2-methyl-2-nitropropyl)-8-(phenylmethoxy)imidazo[1,2-a]pyridine (0.46 g, 1.41 mmol) and acetic acid (6 ml) is heated to 90° C. Powdered iron (0.8 g, 14.3 mmol) in water (3 ml) is added in three portions within 45 minutes. After heating for another 2 hours at 90° C., the solids are removed by filtration and washed with ethanol. The combined filtrates are concentrated under reduced pressure, and the residue is treated with saturated aqueous NaHCO$_3$ solution (50 ml). The aqueous mixture is extracted with ethyl acetate (2×50 ml). The combined organic extracts are dried over magnesium sulfate, and the solvent is removed in vacuo. Chromatography (silica gel, dichloromethane/ethanol 9:1) of the residue gives 113 of the title amine (27%).

Amine 8

A solution of 2-(4-bromo-3-oxo-butyl)-isoindole-1,3-dione (4.1 g, 13.85 mmol) and 2-amino-3-benzyloxypyridine (2.75 g, 13.73 mmol) in ethanol (20 ml) is heated at reflux for 4 hours. After one hour, the desired compound started to precipitate. The mixture is cooled to room temperature and the precipitate is collected by filtration, washed with ethanol and hexane, successively, and dried in vacuo to give 5.43 g of 2-[2-(8-phenylmethoxy-imidazo[1,2-a]pyridin-2-yl) ethyl]-isoindole-1,3-dione (99%).

A mixture of 2-[2-(8-phenylmethoxy-imidazo[1,2-a]pyridin-2-yl)ethyl]-isoindole-1,3-dione (2.9 g, 7.3 mmol) and hydrazine hydrate (1.5 ml) in methanol (25 ml) is heated at reflux for 90 minutes. The formed precipitate is collected by filtration and washed with ethanol. The filtrate is concentrated under reduced pressure to leave another crop of product which is heated with a small amount of ethanol, filtered, and dried in vacuo to give a total of 1.25 g of the title amine (64%).

Amine 9

2-Amino-4-hydroxypyridine is prepared according to a known procedure (Org. Proced. Prep. Int., 29: 117, 1997) and is reacted with 2-bromo-4-methyl-4-nitropentanal (2.19 g, 19.9 mmol) as described for Amine 7. The reaction mixture is concentrated and the residue is treated with ethyl acetate (20 ml), heated and filtered to give 2.79 g of 3-(2-methyl-2-nitropropyl)imidazo[1,2-a]pyridin-7-ol (60%).

3-(2-Methyl-2-nitropropyl)imidazo[1,2-a]pyridin-7-ol (1.5 g, 6.38 mmol), chloroacetamide (1.19 g, 12.73 mmol), potassium carbonate (6.4 mmol) and a small amount of potassium iodide in 2-butanone (30 ml) is heated at reflux overnight. The solids are removed by filtration and the filtrate is concentrated under reduced pressure. The residue is chromatographed on silica gel with dichloromethane/methanol 3:1 to 1:1 to give 640 mg of 2-[3-(2-methyl-2-nitropropyl)imidazo[1,2-a]pyridin-7-yloxy]-acetamide (34%).

The title compound is prepared (87%, 500 mg) from 2-[3-(2-methyl-2-nitropropyl)imidazo[1,2-a]pyridin-7-yloxy]-acetamide (640 mg, 2.19 mmol) by the procedure described for Amine 7, Method A.

Amine 10

2-Amino-4-methylpyridine (2.2 g, 20.3 mmol) and 2-bromo-4-methyl-4-nitropentanal (20.3 mmol) are reacted as described in Amine 7 to give 3.0 g of 7-methyl-3-(2-methyl-2-nitropropyl)imidazo[1,2-a]pyridine (63%).

The title compound is prepared (96%, 2.5 g) from 7-methyl-3-(2-methyl-2-nitropropyl)imidazo[1,2-a]pyridine (3.0 g, 12.9 mmol) by the procedure described for Amine 7, Method A.

Amine 11

2-Amino-5-methoxypyridine (*J. Med. Chem.*, 24:39, 1981; 2.02 g, 16.3 mmol) and 2-bromo-4-methyl-4-nitropentanal (16.3 mmol) are reacted as described in Amine 7 and the product is isolated in two crops from the concentrated mixture by heating twice with dichloromethane (30 ml and 10 ml) and filtration without further chromatographic purification to give 1.71 g of 3-(2-methyl-2-nitropropyl)-6-methoxyimidazo[1,2-a]pyridine (42%).

The title compound is prepared from 3-(2-methyl-2-nitropropyl)-6-methoxyimidazo[1,2-a]pyridine (1.68 g, 6.74 mmol) by the procedure described for Amine 7, method A to give 1.27 g of the title amine (86%).

Amine 12

The trifluoroacetic acid amide protected intermediate is prepared from condensation of (2-amino-3-pyridinyloxy)acetonitrile (J. Gauthier, et al U.S. Pat. No. 4,492,697; J. Gauthier & J. S. Duceppe, *J Hetcyc Chem*, 1984, 21(4), 1081-6) with the α-bromoketone described in the preparation of Amine 1 in 86% yield by essentially following the procedure described for the preparation of Amine 1. This product is deprotected and hydrolyzed with $K_2CO_3$ substantially as described for the preparation of Amine 1 to give the title amine, which is used without chromatographic purification, in 63% yield.

Amine 13

The title amine is prepared from 5-azaindole (M. J. Sloan & R. S. Phillips, *Bioorg Med Chem Lett*, 1992, 2(9), 1053-1056) by essentially following the procedure described for Amine 4.

Amine 14

2-Amino-3-bromopyridine (J. Chem. Soc., Perkin Trans. I, 1999, 1505; 5.0 g, 28.9 mmol) and 2-bromo-4-methyl-4-nitropentanal (28.9 mmol) are reacted as described in Amine 7 to prepare 5.09 g of 8-bromo-3-(2-methyl-2-nitropropyl)imidazo[1,2-a]pyridine (59%).

A mixture of 8-bromo-3-(2-methyl-2-nitropropyl)imidazo[1,2-a]pyridine (1.5 g, 5.0 mmol), $Pd(PPh_3)_4$ (0.68 g), 2M aqueous sodium carbonate solution (8 ml), and dioxane (68 ml) is stirred for 30 minutes under an atmosphere of argon. After addition of thiophene-2-boronic acid (0.96 g, 7.5 mmol), the mixture is stirred overnight at 80° C. The solids are removed by filtration, and the residue is chromatographed (silica gel, dichloromethane/ethanol 95:5) to give 1.52 g of 3-(2-methyl-2-nitropropyl)-8-(2-thienyl)imidazo[1,2-a]pyridine (100%).

The title compound is prepared (92%, 1.26 g) from 3-(2-methyl-2-nitropropyl)-8-(2-thienyl)imidazo[1,2-a]pyridine (1.52 g, 5.04 mmol) by the procedure described for Amine 7, Method A.

Amine 15

8-Bromo-3-(2-methyl-2-nitropropyl)imidazo[1,2-a]pyridine (1.0 g, 3.35 mmol) and 4-trifluoromethyl-benzeneboronic acid (0.96 g, 5.05 mmol) are coupled as described in Amine 14 to give 1.23 g of 3-(2-methyl-2-nitropropyl)-8-(4-trifluoromethyl-phenyl)imidazo[1,2-a]pyridine (100%).

The title compound is prepared (85%, 960 mg) from 3-(2-methyl-2-nitropropyl)-8-(4-trifluoromethyl-phenyl)imidazo[1,2-a]pyridine (1.23 g, 3.38 mmol) by the procedure described for Amine 7, Method A.

Amine 16

8-Bromo-3-(2-methyl-2-nitropropyl)imidazo[1,2-a]pyridine (1.0 g, 3.35 mmol) and 2,4-(bistrifluoromethyl)benzeneboronic acid (1.3 g, 5.04 mmol) are coupled as described in Amine 14 to give 690 mg of 8-(2,4-bistrifluoromethyl-phenyl)-3-(2-methyl-2-nitropropyl)imidazo[1,2-a]pyridine (48%).

The title compound is prepared (79%, 510 mg) from 8-(2,4-bis-trifluoromethyl-phenyl)-3-(2-methyl-2-nitropropyl)imidazo[1,2-a]pyridine (690 mg, 1.6 mmol) by the procedure described for Amine 7, Method A.

Amine 18

2-Amino-3-hydroxypyridine (1.1 g, 10.0 mmol) and 2-bromo-4-methyl-4-nitropentanal (10.0 mmol) are reacted as described in Amine 7 to prepare 1.0 g of 3-(2-methyl-2-nitropropyl)imidazo[1,2-a]pyridin-8-ol (42.5%).

3-(2-Methyl-2-nitropropyl)imidazo[1,2-a]pyridin-8-ol (1.0 g, 4.25 mmol), tert-butyl chloroacetate (964 mg, 6.4 mmol), potassium carbonate (590 mg, 4.27 mmol), and a small amount of potassium iodide in 2-butanone (30 ml) are reacted as described in Amine 9. The crude product residue is chromatographed on silica gel with dichloromethane/ethanol 9:1 to give 1.2 g of tert-butyl [3-(2-methyl-2-nitropropyl)imidazo[1,2-a]pyridin-8-yloxy]-acetate (81%).

The title compound is prepared (89%, 980 mg) from tert-butyl [3-(2-methyl-2-nitropropyl)imidazo[1,2-a]pyridin-8-yloxy]-acetate (1.2 g, 3.43 mmol) by the procedure described for Amine 7, Method A.

Amine 19

A mixture of 3-hydroxy picolinic amide (10 g, 72 mmol), ethyl bromoacetate (12.02 g, 72 mmol) and anhydrous potassium carbonate (10.9 g, 79.2 mmol) in 250 ml of dry 2-butanone is heated at 80° C. for 20 hours. After cooling, the inorganic salts are filtered off and the filtrate is reduced to approximately 120 ml. After addition of cold t-butyl methyl ether the resulting precipitate is filtered off, rinsed with cold t-butyl methyl ether and dried to give 8.6 g of 3-(ethoxycarbonylmethoxy)picolinamide (53%).

To a solution of 3-(ethoxycarbonylmethoxy)picolinamide (5.1 g, 22.8 mmol) and triethylamine (6.68 ml, 47.9 mmol) in 100 ml of dry methylene chloride is added trifluoroacetic anhydride (6.77 ml, 47.9 mmol), dropwise, at ambient temperature under argon. After stirring for 16 hours, 100 ml of water is added. The organic phase is separated and washed with aqueous sodium hydrogen carbonate to neutral pH. After drying over sodium sulfate and evaporation, the residue is purified via flash chromatography on silica gel using a methylene chloride-ethanolic ammonia gradient (99:1 to 95:5) to give 3.90 g of 2-cyano-3-(ethoxycarbonylmethoxy)pyridine (87%).

To a solution of 2-cyano-3-(ethoxycarbonylmethoxy)pyridine (3.2 g, 15.52 mmol) in 180 ml of ethanol is added concentrated aqueous HCl (2.92 ml, 35 mmol) and 10% palladium on charcoal (1.5 g). After stirring for 4 hours under a hydrogen pressure of 4 bar, the mixture is filtered through celite, rinsed with ethanol and evaporated. The 2-aminomethyl-3-(ethoxycarbonylmethoxy)pyridine dihydrochloride thus obtained is sufficiently pure and used in the next step without further purification. Yield: 3.82 g (100%).

To a solution of 2-aminomethyl-3-(ethoxycarbonyl-methoxy)pyridine dihydrochloride (610 mg, 2.155 mmol), triethylamine (732 µl, 5.258 mmol), N,N-dicyclohexylcarbodiimide (596 mg, 2.892 mmol) and 4-(N,N-diemethylamino)-pyridine (10 mg) in 6 ml of dry methylene chloride is added β,β-dimethyl-1,3-dioxo-2-isoindolinepropionic acid (650 mg, 2.629 mmol) at ambient temperature. The mixture is stirred for 24 hours. The precipitate of dicyclohexyl urea is filtered off. The filtrate is evaporated and the residue is purified via flash chromatography on silica gel using a methylene chloride/methylene chloride-ethanolic ammonia gradient (100 to 97:3) to give 591 mg of (2-{[3-(1,3-dioxo-1,3-dihydro-isoindol-2-yl)-3-methyl-butyrylamino]-methyl}-pyridin-3-yloxy)-acetic acid ethyl ester (46%).

A solution of (2-{[3-(1,3-dioxo-1,3-dihydro-isoindol-2-yl)-3-methyl-butyrylamino]-methyl}-pyridin-3-yloxy)-acetic acid ethyl ester (2.79 g, 6.349 mmol) in 100 ml of neat phosphoryl chloride is stirred at 75° C. for 16 hours. The reaction mixture is poured on 200 g of crushed ice and extracted with methylene chloride. The organic phase is dried over sodium sulfate and evaporated. The residue is purified via flash chromatography on silica gel using a methylene chloride/methylene chloride-ethanolic ammonia gradient (100 to 96:4) to give 1.48 g of {3-[2-(1,3-dioxo-1,3-dihydro-isoindol-2-yl)-2-methyl-propyl]-imidazo[1,5-a]pyridin-8-yloxy}-acetic acid ethyl ester (55%).

To a solution of {3-[2-(1,3-Dioxo-1,3-dihydro-isoindol-2-yl)-2-methyl-propyl]-imidazo[1,5-a]pyridin-8-yloxy}-acetic acid ethyl ester (1.48 g, 3.50 mmol) in 30 ml of ethanol is added hydrazine hydrate (0.7 ml, 14 mMol) and the mixture is heated to 80° C. for 15 minutes in a microwave oven (MLS ETHOS 1600). The reaction mixture is evaporated. Flash chromatography of the residue on silica gel using methylene chloride-ethanolic ammonia (80:20) yielded an equimolar mixture of the title amine and the corresponding 2-carbonyl hydrazide benzamide. This mixture is further hydrolyzed with 5N HCl in isopropanol for 16 hours at 70° C. The mixture is evaporated and the residue is treated with 5 ml of ethanolic ammonia. After repeated evaporation, flash chromatography on silica gel using a methylene chloride/methylene chloride-ethanolic ammonia gradient (100 to 90:10) gives 340 mg of the title amine (33%) slightly contaminated with traces of the corresponding i-propyl ester.

Amine 20

2-Aminopyridine (1.3 g, 13.8 mmol) and 2-bromo-4-methyl-4-nitropentanal (3.1 g, 13.8 mmol) are reacted as described in Amine 7 to prepare 2.59 g of 3-(2-methyl-2-nitropropyl)imidazo[1,2-a]pyridine (85%).

The title compound is prepared (96%, 990 mg) from 3-(2-methyl-2-nitropropyl)imidazo[1,2-a]pyridine (1.2 g, 5.47 mmol) by the procedure described for Amine 7, Method A.

Amine 21

8-Bromo-3-(2-methyl-2-nitropropyl)imidazo[1,2-a]pyridine (1.0 g, 3.35 mmol) and thiophene-3-boronic acid (0.64 g, 5.0 mmol) are coupled as described in Amine 14 to give 760 mg of 3-(2-methyl-2-nitropropyl)-8-(3-thienyl)imidazo[1,2-a]pyridine (75%).

The title compound is prepared from 3-(2-methyl-2-nitropropyl)-8-(3-thienyl)imidazo[1,2-a]pyridine (760 mg, 2.52 mmol) by the procedure described for Amine 7, method A to give 400 mg of the title amine (58%).

Amine 22

The title amine is prepared from 5-azaindole (M. J. Sloan & R. S. Phillips, *Bioorg Med Chem Lett*, 1992, 2(9), 1053-1056) by essentially following the procedure described for Amine 4.

Amine 23

3-(2-methyl-2-nitropropyl)imidazo[1,2-a]pyridin-8-ol (1.0 g, 4.25 mmol), chloroacetamide (598 mg, 6.4 mmol), potassium carbonate (885 mg, 6.4 mmol), and a small amount of potassium iodide in butanone (30 ml) are reacted and the product, 115 mg of 2-[3-(2-methyl-2-nitropropyl) imidazo[1,2-a]pyridin-8-yloxy]-acetamide, is purified as described in Amine 18 (9.3%).

The title compound is prepared (100%, 103 mg) from 2-[3-(2-methyl-2-nitropropyl)imidazo[1,2-a]pyridin-8-yloxy]-acetamide (115 mg, 0.39 mmol) by the procedure described for Amine 7, Method A.

Amine 24

3-(2-methyl-2-nitropropyl)imidazo[1,2-a]pyridin-8-ol (1.0 g, 4.25 mmol), 2-chloronicotinamide (1.0 g, 6.4 mmol), potassium carbonate (885 mg, 6.4 mmol), and a small amount of potassium iodide in 2-butanone (30 ml) are reacted and the product, 490 mg of 2-[3-(2-methyl-2-nitropropyl)imidazo[1,2-a]pyridin-8-yloxy]-pyridin-3-carboxamide, purified as described in Amine 18 (9.3%).

The title compound is prepared (100%, 450 mg) from 2-[3-(2-methyl-2-nitropropyl)imidazo[1,2-a]pyridin-8-yloxy]-pyridin-3-carboxamide (490 mg, 1.38 mmol) by the procedure described for Amine 7, Method A.

Amine 25

The title compound is prepared (99%, 1.04 g) from 3-(2-methyl-2-nitropropyl)imidazo[1,2-a]pyridin-8-ol (1.2 g, 5.10 mmol) by the procedure described for Amine 7, method A to give 1.04 g of the title amine (99%).

Boronic Acids

Boronic Acids 1 and 2 are obtained from commercial sources for use as described in Scheme 2. These boronic acids are pictured below in Table 3.

TABLE 3

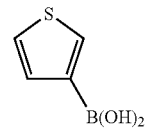

1

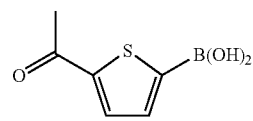

2

Aryl Halides of Formula V

Aryl Halide 1

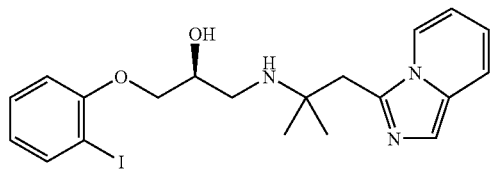

A solution of Epoxide 22 (496 mg, 1.69 mmol) and Amine 6 (410 mg, 1.69 mmol) in dry ethanol (10 ml) is heated at 110° C. overnight. After evaporation of the solvent, the residue is purified via flash chromatography (silica gel, dichloromethane/ethanol 95:5 to 85:15) to give 150 mg of the title compound (17%). MS m/e=538.2 (M$^+$+1).

EXAMPLES

Representative Procedure 1: Amination of Epoxide

A vial is charged with a solution of single amine of formula III (0.2M in ethanol or t-butanol, 90 micromolar) and a solution of a single epoxide of formula II (0.2M in dimethylsulfoxide, 80 micromolar). The vial is sealed and heated to 80° C. for 24-48 hours. The solution is cooled to room temperature, diluted with methanol, and passed over a cation exchange column, eluting the basic material with 1N methanolic ammonia.

Representative Procedure 2: Amination of Epoxide

A stirred mixture of an epoxide of formula II (1 equivalent) and an amine of formula III (1-2 equivalents) in ethanol, methanol, n-butanol or t-butanol is heated at 70-80° C. for 2-72 hours. The solvent is evaporated to dryness to give a crude oil that is optionally diluted with methanol or ethanol and passed over a cation exchange column (eluting the free base product with 1N methanolic ammonia) before further purification.

The final products prepared via Representative Procedure 1 or 2 may be further purified by flash or radial chromatography. Typical chromatography conditions include: a) using a variable mixture of 25:5:1 chloroform/methanol/ammonium hydroxide and 9:1 chloroform/methanol; b) a variable mixture of 90:10:1 $CH_2Cl_2$/ethanolic $NH_3$ gradient; c) dichloromethane/6-12% methanol, 0.15-0.35M ammonia in dichloromethane gradient; d) methylene chloride with a step gradient to 2-8% methanol; e) chloroform/2.0M ammonia in methanol, from 0-10% to 5-20% gradient elution or f) isocratic 6-8% 2M ammonia in methanol: 92-94% dichloromethane.

Alternatively, the final products may be purified on C18 bonded silica gel using either mass guided or UV guided reverse phase liquid chromatography (acetonitrile/water with 0.01% hydrochloric acid or 0.1% trifluoroacetic acid). When purification of a compound of the present invention results in production of a free base, the free base thus prepared may be salified, e.g., by dissolution of the free base in $CH_2Cl_2$ or diethylether, adding 1M ethanolic HCl or a solution of HCl in diethylether, and evaporating the volatiles, or as described in more detail below.

For example, a hydrochloride salt may be prepared by dissolving the free base in dichloromethane, diethylether, or a mixture of ethyl acetate and methanol and adding 1M ethanolic HCl, a solution of HCl in diethylether, or 0.5M ammonium chloride in methanol. The resulting mixture is allowed to stir for a short time, e.g., for five minutes, before evaporating the volatiles and optionally triturating in diethyl ether to give the hydrochloride salt.

The oxalate salts may be prepared by dissolving the free base in a small amount of ethyl acetate, optionally adding methanol for solubility. The resulting solution is treated with 1 equivalent of a 0.5M solution of oxalic acid in ethyl acetate. The reaction mixture is either concentrated in vacuo or centrifuged, separated, and the solids are dried, to give the oxalate salt.

To prepare a succinate salt, the free base may be dissolved in a small amount of ethyl acetate or methanol and then treated with 1 equivalent of succinic acid in methanol. The resulting slurry is dissolved in the minimum amount of methanol then concentrated in vacuo to give the succinate salt.

The table below sets out representative combinations of Amines and Epoxides that are reacted as described in Representative Procedure 1 or 2. Preparation of desired product is confirmed via mass spectral analysis (MSA). Emax±Standard Error Mean (SEM) data, discussed in the "Demonstration of Function" section below, is also included for said compounds where available. The Emax values represent the average of at least 3 runs except as otherwise indicated.

TABLE 3

| E.g. | Epoxide | Amine | MSA | Isolated Form | Emax (%) ± SEM |
|---|---|---|---|---|---|
| 1 | 1 | 1 | 422.2 | Hydrochloride | 50.8 ± 0.4 |
| 2 | 1 | 3 | 422.2 | Hydrochloride | 58.6 ± 3.4 |
| 3 | 1 | 4 | 422.2 | Hydrochloride | 66.9 ± 2.1 |
| 4 | 1 | 5 | 436.2 | Hydrochloride | 50.2 ± 2.3 |
| 5 | 1 | 6 | 408.2 | Hydrochloride | 42.2 ± 2.5 |
| 6 | 1 | 7 | 528.2 | Hydrochloride | 67.8 ± 3.9 |
| 7 | 1 | 9 | 495.4 | Trifluoroacetate | 37.4 ± 5.9 |
| 8 | 1 | 10 | 436.2 | Hydrochloride | 90.6 ± 4.4 |
| 9 | 1 | 11 | 452.2 | Free Base | 66.7 ± 3.7 |
| 10 | 1 | 12 | 496.2 | Hydrochloride | 73.3 ± 2.0 |
| 11 | 1 | 13 | 422.2 | Hydrochloride | 59.0 ± 6.2 |
| 12 | 1 | 14 | 504.0 | Hydrochloride | 62.2 ± 7.5 |
| 13 | 1 | 15 | 566.2 | Hydrochloride | 53.1 ± 1.8 |
| 14 | 1 | 16 | 634.0 | Hydrochloride | 80.0 ± 5.7 |
| 15 | 1 | 20 | 422.2 | Hydrochloride | 51.2 ± 4.0 |
| 16 | 1 | 21 | 504.2 | Hydrochloride | 63.0 ± 0.7 |
| 17 | 1 | 22 | 422.2 | Hydrochloride | 59.9 ± 0.8 |
| 18 | 1 | 23 | 495.4 | Hydrochloride | 70.9 ± 1.0 |
| 19 | 1 | 24 | 557.8 | Hydrochloride | 88.4 ± 3.0 |
| 20 | 2 | 3 | 405.2 | Hydrochloride | 42.7 ± 2.8 |
| 21 | 2 | 10 | 419.2 | Hydrochloride | 62.1 ± 1.4 |
| 22 | 2 | 11 | 435.2 | Trifluoroacetate | 37.1 ± 1.7 |
| 23 | 3 | 1 | 407.2 | Hydrochloride | 36.7 ± 1.6 |
| 24 | 3 | 2 | 379.4 | Trifluoroacetate | 10.0 ± 0.0 |
| 25 | 3 | 3 | 430.0 | Hydrochloride | 53.7 ± 1.9 |
| 26 | 3 | 4 | 407.2 | Hydrochloride | 65.6 ± 1.8 |
| 27 | 3 | 8 | 485.3 | Hydrochloride | 18.3 ± 3.3 |
| 28 | 3 | 10 | 421.2 | Hydrochloride | 61.6 ± 0.3 |
| 29 | 3 | 12 | 481.2 | Hydrochloride | 51.0 ± 4.4 |
| 30 | 3 | 14 | 489.2 | Trifluoroacetate | 64.4 ± 5.8 |
| 31 | 3 | 15 | 551.4 | Hydrochloride | 45.2 ± 1.0 |
| 32 | 3 | 16 | 619.4 | Hydrochloride | 68.0 ± 5.1 |
| 33 | 3 | 20 | 407.4 | Hydrochloride | 42.9 ± 2.0 |
| 34 | 3 | 21 | 489.2 | Hydrochloride | 43.4 ± 2.0 |
| 35 | 3 | 24 | 543.2 | Hydrochloride | 68.9 ± 4.7 |
| 36 | 3 | 25 | 423.2 | Hydrochloride | 46.8 ± 5.5 |
| 37 | 4 | 3 | 407.2 | Hydrochloride | 25.4 ± 5.0 |
| 38 | 5 | 3 | 447.0 | Hydrochloride | 67.5 ± 4.3 |
| 39 | 6 | 3 | 436.0 | Hydrochloride | 62.9 ± 3.3 |
| 40 | 5 | 19 | 549.2 | Hydrochloride | 76.5 ± 2.6 |

Example 41

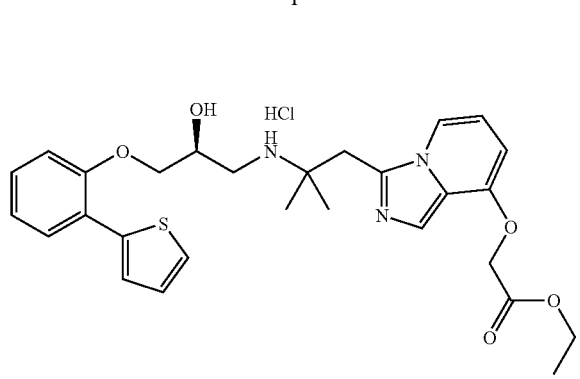

A vial is charged with a solution of Amine 19 (0.2M in t-butanol, 300 micromolar) and a solution of Epoxide 1 (0.2M in dimethylsulfoxide, 300 micromolar). The vial is sealed and heated to 80° C. for 16 hours. The solution is cooled to room temperature, and passed over a cation exchange column, removing the impurities by eluting with methanol, and eluting the product with 1N methanolic ammonia. Under these chromatography conditions the product ester is hydrolyzed (about 66%) to the corresponding acid. Further purification of the mixture is achieved by flash chromatography on silica gel using a methylene chloride/ethanolic ammonia gradient (100 to 95/5. The desired fractions are evaporated, dissolved in a small volume of methylene chloride and treated with excess 1N ethanolic HCl. After evaporation of the volatiles the hydrochlorides of the title compounds are obtained. MSA 495.2/524.2.

Example 42

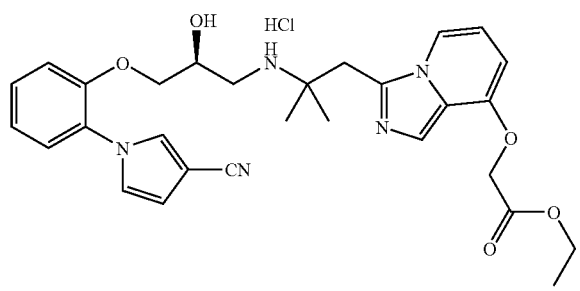

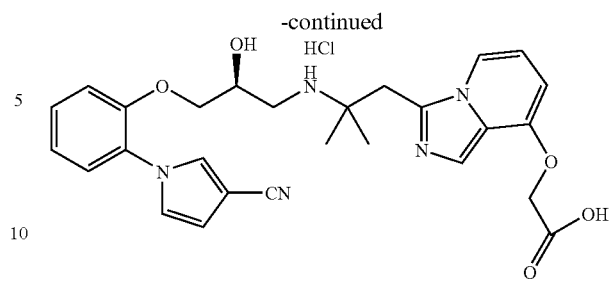

Amine 19 and Epoxide 4 are reacted as described above for Example 42 to prepare a mixture of the title compounds. MSA 503.2/532.2.

Example 43

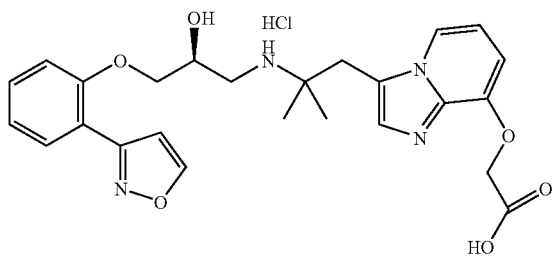

A vial is charged with a solution of Amine 18 (319 mg, 1 mmol) and Epoxide 3 (217 mg, 1 mmol) in 5 ml of ethanol. The vial is sealed and heated to 85° C. for 16 hours. The solution is cooled to room temperature and concentrated under reduced pressure. Purification of the mixture is achieved by HPLC on a Hyperprep column C-18 using a water/acetonitrile gradient (9:1 up to 100% acetonitrile) containing 0.1% trifluoroacetic acid. The desired fractions are evaporated, dissolved in a small volume of dichloromethane and treated with excess 1N ethanolic HCl. After evaporation of the volatiles the title compound is obtained; MSA 481.2; yield: 39.3 mg (7.6%).

Representative Procedure 3: Suzuki Coupling

Procedure 3(a)

A compound of formula V (6.4 mmol) is dissolved in 50 ml of dry dioxane and thoroughly flushed with argon. Palladium(0) tetrakis(triphenylphosphine) (750 mg, 0.64 mmol) is added under argon and stirred at ambient temperature until the mixture becomes homogenous. The clear solution is divided into aliquots of 2 ml, and each testing tube is charged with 2 equivalents of an aryl boronic acid and 500 microliters of 2M aqueous sodium carbonate under argon. The testing tubes are sealed and heated in a microwave oven (MLS ETHOS 1600) for 35 minutes and 100° C. at 1000 W. After complete conversion the samples are diluted with 2 ml of water and extracted with 3 ml of dichloromethane. Extraction is repeated with 2 ml of dichloromethane. The organic solutions are collected and dried over sodium sulfate. The organic filtrate is treated with pre-treated Amberlyst 15 (3 to 4 g each). (Prior to use Amberlyst 15 is prewashed with dichloromethane, ethanol then dichloromethane until the filtrate is colorless). The suspensions are shaken for 30 minutes on an orbital shaker and filtered. The Amberlyst is repeatedly rinsed with dichloromethane/ethanol 1:1 (4×3 ml) and then repeatedly treated with dichloromethane/ethanolic ammonia 1:1. Finally the resin is treated with ethanolic ammonia overnight. The alkaline filtrates are collected and evaporated.

Procedure 3(b)

A mixture of an aryl halide of formula V (1.2 mmol), a boronic acid (2.4 mmol), palladium(0) tetrakis(triphenylphosphine) (0.06 mmol), and 2M aqueous sodium carbonate (1.5 ml) in dioxane (20 ml) is heated overnight at 100° C. in a sealed tube. The mixture is poured into water and extracted two times with ethyl acetate. The combined organic layers are washed with brine, dried over sodium sulfate, and concentrated under reduced pressure.

The final products prepared via Suzuki coupling may be purified by normal phase chromatography (silica gel, dichloromethane/ethanolic ammonia) providing the free bases or by reverse phase chromatography (acetonitrile/0.1% trifluoroacetic acid or 0.01% HCl in water) providing the trifluoroacetate or hydrochloride salts. The final products existing as salts may also be prepared in a separate salification step by dissolution of the free base in ethanol or dichloromethane and treatment of the solution with acid, e.g., 1N ethanolic HCl. Removal of all volatiles under reduced pressure, affords the desired salt.

The table below sets out representative combinations of aryl halides and boronic acids that are reacted as described above in Representative Procedure 3(a) or 3(b).

TABLE 4

| E.g. | Aryl Halide | Boronic Acid | MSA | Isolated Form | Emax (%) ± SEM |
|---|---|---|---|---|---|
| 44 | 1 | 1 | 422.2 | Hydrochloride | 44.5 ± 4.1 |
| 45 | 1 | 2 | 464.3 | Free Base | 63.5 ± 2.4 |

Demonstration of Function

The genes encoding the human $\beta_1$-adrenergic receptor (Frielle et al., *Proc. Natl. Acad. Sci.*, 84:7920-7924, 1987), the human $\beta_2$-adrenergic receptor (Kobika et al., *Proc. Natl. Acad. Sci.*, 84:46-50, 1987, Emorine et al., *Proc. Natl. Acad. Sci.*, 84:6995-6999, 1987) and the human β3 adrenergic receptor (Granneman et al., *Molecular Pharmacology*, 44(2):264-70, 1993) are individually subcloned into a phd expression vector (Grinnell et al., *Bio/Technology*, 5:1189-1192, 1987) and transfected into the DXB-11 Chinese hamster ovary (CHO) cell line by calcium phosphate precipitation methodology. The stably transfected cells are grown to 95% confluency in 95% Dulbecco's modified Eagles Medium (DMEM), 5% fetal bovine serum and 0.01% proline. Media is removed and the cells are washed with phosphate buffered (pH 7.4) saline (without magnesium and calcium). Cells are then lifted using an enzyme free cell dissociation solution (Specialty Media, Lavallette, N.J.) and pelleted by centrifugation.

Cells from each of the above cell lines are resuspended and added (20,000/well) to a 96-well plate. Cells are incubated at 37° C. with representative compounds of the invention for 20 minutes in buffer (Hank's balanced salt solution, 10 mM HEPES, 0.1% BSA, 1 mM L-ascorbic acid, 0.2% dimethyl sulfoxide, 1 mM 3-isobutyl-1-methylxanthine, pH 7.4). After halting the incubation with quench buffer (50 mM Na Acetate, 0.25% Triton X-100, pH 5.8), the c-AMP level is quantified by scintillation proximity assay (SPA) using a modification of the commercially available c-AMP kit (Amersham, Arlington Heights, Ill.) with rabbit anti-cAMP antibody (ICN Biomedicals, Aurora, Ohio) for the kit.

Sigmoidal dose response curves, from the whole cell receptor coupled c-AMP assay are fit to a four parameter logistic equation using non linear regression: $y=(a-d)/(1+(Dose/c)^b)+d$ where a and d are responses at zero and maximal dose, b is the slope factor and c is the $EC_{50}$ as previously described (DeLean et al., *Am. J. Physiol.*, 235, E97-E102, 1978). $EC_{50}$ is assessed as the concentration producing 50% of the maximum response to each agonist.

Isoproterenol is accepted in the art as a non-selective $\beta_3$ agonist and is widely used as a comparator in evaluating the activity of compounds. See *Trends in Pharm. Sci.*, 15:3, 1994. The % intrinsic activity (Emax) of representative compounds of the invention is assessed relative to isoproterenol by the compound's maximal response divided by the isoproterenol maximal response times 100.

In Vitro Rat Atrial Tachycardia

Male rats (250-350 g) (Harlan Sprague Dawley, Indianapolis, Ind., USA) are killed by cervical dislocation. Hearts are removed and the left and right atria are dissected and mounted with thread in tissue baths containing 10 mls of modified Krebs' solution. Initial resting tension is 1.5-2.0 g at the outset of the experiment (*Naunyn-Schmied Arch. Pharmacol.*, 320:145, 1982). Tissues are allowed to equilibrate approximately 30 minutes with vigorous oxygenation before exposure to a compound of the invention.

To evaluate the ability of test compounds to increase heart rate, representative compounds of the present invention are added cumulatively once the atrial rate reaches a steady state from the previous addition. Compound addition is continued until no further increase in atrial rate occurs or until a concentration of $10^{-4}$M is reached. The increase in beats per minute (bpm) is measured for each concentration of test compound by means of a BioPac System (*Br. J. of Pharmacol.*, 126:1018-1024, 1999).

Utilities

As agonists of the $\beta_3$ receptor, a compound of the present invention is useful in treating conditions in human and non-human animals in which the $\beta_3$ receptor has been demonstrated to play a role.

The diseases, disorders or conditions for which compounds of the present invention are useful in treating or preventing include, but are not limited to, (1) diabetes mellitus, (2) hyperglycemia, (3) obesity, (4) hyperlipidemia, (5) hypertriglyceridemia, (6) hypercholesterolemia, (7) atherosclerosis of coronary, cerebrovascular and peripheral arteries, (8) gastrointestinal disorders including peptid ulcer, esophagitis, gastritis and duodenitis, (including that induced by H. pylori), intestinal ulcerations (including inflammatory bowel disease, ulcerative colitis, Crohn's disease and proctitis) and gastrointestinal ulcerations, (9) neurogenic inflammation of airways, including cough, asthma, (10) depression, (11) prostate diseases such as benign prostate hyperplasia, (12) irritable bowel syndrome and other disorders needing decreased gut motility, (13) diabetic retinopathy, (14) neuropathic bladder dysfunction, (15) elevated intraocular pressure and glaucoma and (16) non-specific diarrhea dumping syndrome.

Human patients in need of obesity treatment are typically those with a body mass index (BMI)>27 or those with a BMI≧25 when co-morbidities, e.g., hypertension, sleep apnea and/or osteoarthritis, are present. A patient population at particular need of treatment are those with a BMI>30 or >27 with co-morbities.

Human patients in need of hypertension treatment are frequently overweight individuals, i.e., those with a BMI≧25, but may also be of normal body weight (i.e., BMI<25).

Human patients in need of type 2 diabetes treatment are typically individuals with a BMI<25, i.e., individuals that are not overweight.

Formulation

The compound of formula I is preferably formulated in a unit dosage form prior to administration. Therefore, yet another embodiment of the present invention is a pharmaceutical formulation comprising a compound of formula I and a pharmaceutical carrier.

The present pharmaceutical formulations are prepared by known procedures using well-known and readily available ingredients. In making the formulations of the present invention, the active ingredient (formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

Formulation Examples

Formulation 1

| Tablets | |
|---|---|
| Ingredient | Quantity (mg/tablet) |
| Active Ingredient | 5-500 |
| Cellulose, microcrystalline | 200-650 |
| Silicon dioxide, fumed | 10-650 |
| Stearate acid | 5-15 |

The components are blended and compressed to form tablets.

Formulation 2

| Suspensions | |
|---|---|
| Ingredient | Quantity (mg/5 ml) |
| Active Ingredient | 5-500 mg |
| Sodium carboxymethyl cellulose | 50 mg |
| Syrup | 1.25 mg |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Formulation 3

| Intravenous Solution | |
|---|---|
| Ingredient | Quantity |
| Active Ingredient | 25 mg |
| Isotonic saline | 1,000 ml |

The solution of the above ingredients is intravenously administered to a patient at a rate of about 1 ml per minute.

Dose

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. However, it will be understood that the therapeutic dosage administered will be determined by the physician in the light of the relevant circumstances.

Generally, an effective minimum daily dose of a compound of formula I is about 5, 10, 15, or 20 mg. Typically, an effective maximum dose is about 500, 100, 60, 50, or 40 mg. Most typically, the dose ranges between 15 mg and 60 mg. The exact dose may be determined, in accordance with the standard practice in the medical arts of "dose titrating" the recipient; that is, initially administering a low dose of the compound, and gradually increasing the dose until the desired therapeutic effect is observed.

Route of Administration

The compounds can be administered by a variety of routes including the oral, rectal, transdermal, subcutaneous, topical, intravenous, intramuscular or intranasal routes.

Combination Therapy

A compound of formula I may be used in combination with other drugs that are used in the treatment/prevention/suppression or amelioration of the diseases or conditions for which compounds of formula I are useful, e.g., treatment of obesity and/or type 2 diabetes. Such other drug(s) may be administered, by a route and in an amount commonly used therefor, contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those that also contain one or more other active ingredients, in addition to a compound of formula I.

We claim:

1. A compound of the formula:

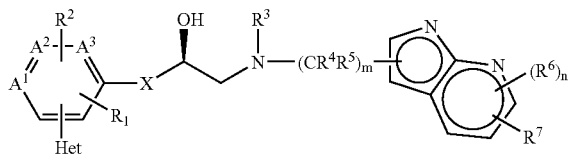

wherein:
- m is 2;
- n is 0 or 1;
- $A^1$, $A^2$ and $A^3$ are carbon;
- Het is at the ortho position relative to X and is thien-2-yl optionally substituted with CN or $CH_3$;
- $R^1$, $R^2$ and $R^3$ are H;
- $R^4$ and $R^5$ are independently H or methyl at each occurrence;
- $R^6$ is independently at each occurrence methyl;
- $R^7$ is at the 6- or 7-position of the 6,5 ring system to which it is attached and is selected from H, $O(CH_2)_pR^{12}$ or thienyl;
- X is $OCH_2$;
- p is 0 or 1; and
- $R^{12}$ is $CONH_2$, phenyl or pyridyl substituted once with $CONH_2$; or a pharmaceutical salt thereof.

2. A compound which is:

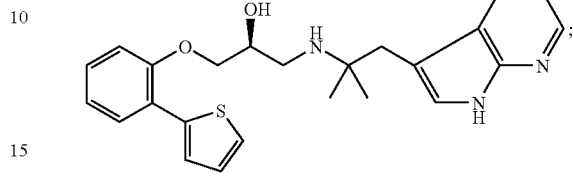

or a pharmaceutical salt thereof.

3. The compound of claim 1 which is the hydrochloride salt.

4. A pharmaceutical formulation comprising a compound of claim 1 and a pharmaceutical carrier.

5. A method of treating Type 2 Diabetes comprising administering to a patient in need thereof a compound of claim 1.

6. A method of treating obesity comprising administering to a patient in need thereof an effective amount of a compound of claim 1.

* * * * *